United States Patent [19]

Popescu et al.

[11] Patent Number: 4,981,692

[45] Date of Patent: Jan. 1, 1991

[54] THERAPEUTIC TREATMENT BY INTRAMAMMARY INFUSION

[75] Inventors: Mircea Popescu; Christine E. Swenson, both of Plainsboro; Sterling C. Johnson, Skillman; Robert P. Lenk, Lambertville, all of N.J.

[73] Assignee: The Liposome Company, Inc., Princeton, N.J.

[21] Appl. No.: 86,467

[22] Filed: Aug. 18, 1987

Related U.S. Application Data

[63] Continuation-in-part of Ser. No. 946,398, Dec. 23, 1986, and a continuation-in-part of Ser. No. 660,573, Oct. 12, 1984, which is a continuation-in-part of Ser. No. 476,496, Mar. 24, 1983, Pat. No. 4,522,803.

[51] Int. Cl.$^5$ .................... A61K 9/127; A61K 37/22; A61K 45/05
[52] U.S. Cl. .................... 424/422; 424/480; 428/402.2; 514/37; 514/885
[58] Field of Search ............ 428/402.2; 424/450, 424/422; 436/829; 514/37, 885

[56] References Cited

U.S. PATENT DOCUMENTS

| | | |
|---|---|---|
| 660,573 | 10/1984 | Lenk et al. . |
| 946,391 | 12/1986 | Bally et al. . |
| 946,398 | 12/1986 | Lenk et al. . |
| 4,438,052 | 3/1984 | Weder et al. .......................... 264/4.6 |
| 4,460,577 | 7/1984 | Moro et al. ........................... 424/79 X |
| 4,522,803 | 6/1985 | Lenk et al. .................... 428/402.2 X |
| 4,565,696 | 1/1986 | Heath et al. .......................... 514/2 X |
| 4,731,210 | 3/1988 | Weder et al. .......................... 264/4.3 |

OTHER PUBLICATIONS

D. C. Blood et al.: *Veterinary Medicine,* Fifth Edition, Lea & Febiger, Philadelphia (1979), pp. 500–505.
Dees et al., *Vet Immunol. and Immunopath.,* 1985, 8:171–182, "Enhanced Intraphagocytic Killing of *Brucella abortus,* in Bovine Mononuclear Cells by Liposomes–Containing Gentamicin".
Feiz, et al., *Br. J. Clin. Pract.,* 1973, 27:410–413, "A Comparative Study of Therapeutic Agents Used for Treatment of Acute Brucellosos".
Fountain, et al., *J. Infect Dis.,* 1985, 152:529–535, "Treatment of *Brucella Canis* and *Brucella abortus* in *vitro,* by Stable Plurilamellar Vesicle-Encapsulated Aminoglycosides".
Herrell, et al., *Postgrad Med,* 1952, 11:476–486, "Treatment of Brucellosis with Aereomycin or Terramycim combined with Dihydrostreptomycin".
Milward, et al., *Am. J. Vet. Res.,* 1984, 45:1825–1828, "Effectiveness of Various Therapeutic Regimens for Bovine brucellosis".
Nicoletti, et al., *J. Am. Vet Med Assoc.,* 1985, 187:493–495, "Efficacy of Longacting Oxtetracyclene Alone or in Combination with Streptomycin in the Treatment of Bovine brucellosis".
Phillippon, et al., *Ann. Rech. Vet.,* 1970, 1:203–213, "Brucellose Bovine Experimentale: II Repartition de *Brucella abortus* dans l'Organisme Six Semaines apres le Part et Trois Mois a Cinq Mois et Demi apres l'Epreure Infectante".
Popescu, et al., *Liposomes: From Biophysics to Therapeutics,* 1987, 219–252, "Liposome–Mediated Treatment of Viral, Bacterial and Protozoal Infections".
Quelch, et al., *Am. J. Vet. Res.,* 1984, 45:1409–1412, "Enhanced Uptake of Liposome by Bovine Macrophages after Opsonization with Antibotics to Brucella abortus".

*Primary Examiner*—Richard D. Lovering
*Attorney, Agent, or Firm*—Allen Bloom; Thomas M. Saunders; Ronald G. Ort

[57] ABSTRACT

A method of treating, by intramammary infusion of liposomes, *Brucella spp.* infections in an animal by administration of a therapeutically effective amount of aminoglycoside in liposome form, also being a method of administering a therapeutic agent in liposome form to a proximal mammary lymph node or mammary tissue of an animal.

21 Claims, 3 Drawing Sheets

A: CONTROL
B: BUFFER-FILLED SPLV'S
C: STREPTOMYCIN
D: SPLV- ENTRAPPED STREPTOMYCIN

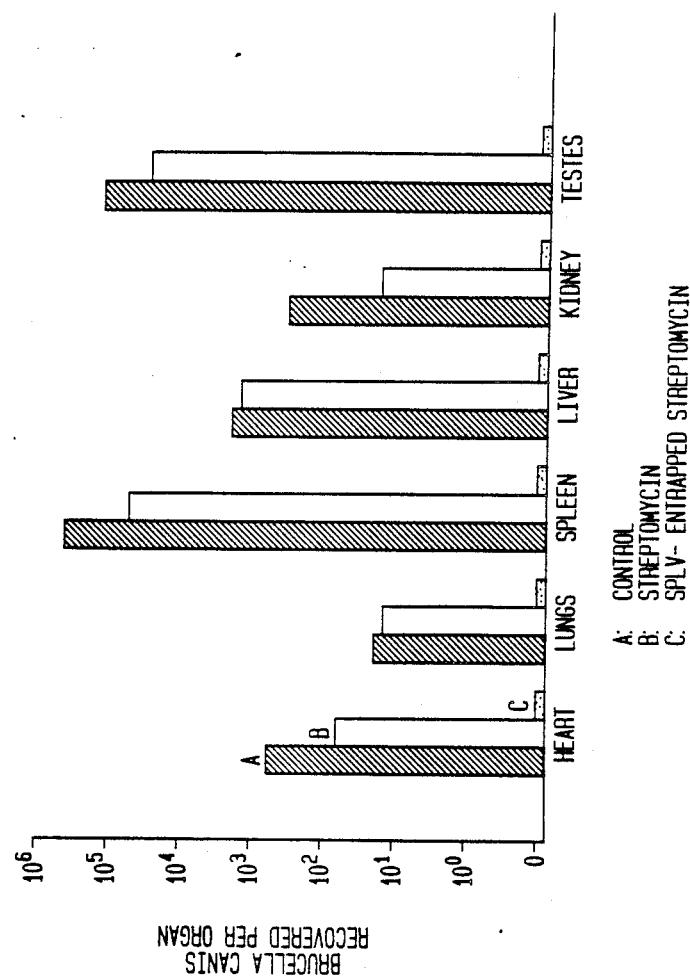

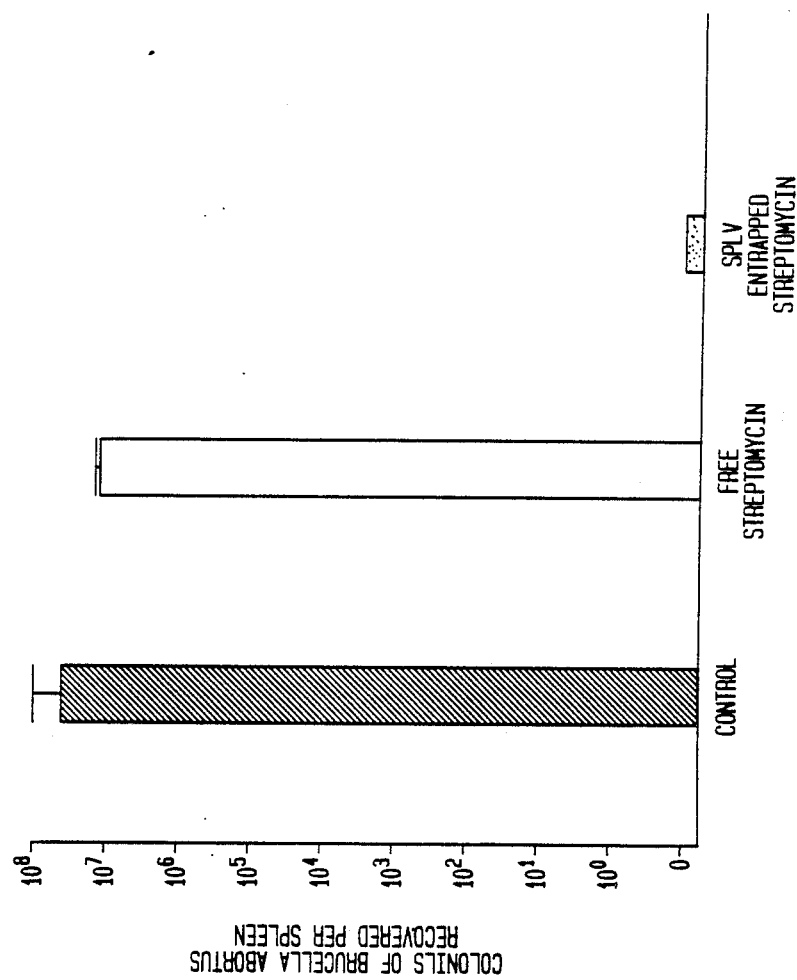

THERAPEUTIC TREATMENT BY INTRAMAMMARY INFUSION

The present invention is a continuation-in-part of copending U.S. patent application Ser. No. 946,398, filed Dec. 23, 1986, and copending U.S. patent application Ser. No. 660,573 filed Oct. 12, 1984 which is in turn a continuation-in-part of U.S. patent application Ser. No. 476,496 filed Mar. 24, 1983 and now U.S. Pat. No. 4,522,803 to Lenk et. al issued June 11, 1985.

FIELD OF THE INVENTION

The present invention concerns a method of treating, by intramammary infusion of liposomes, Brucella spp. infections in an animal by administration of a therapeutically effective amount of aminoglycoside in liposome form, also being a method of administering a therapeutic agent to a proximal mammary lymph node or mammary tissue of an animal.

BACKGROUND OF THE INVENTION

Many workers have attempted to develop an effective and practical chemotherapeutic regimen for brucellosis in animals, including humans, and particularly in dairy animals such as camels, cows, sheep and goats. The goal has been to salvage farm animals with superior production and breeding potential. Furthermore in many countries the slaughter of infected animals is not possible for financial reasons and healthy replacements may not be available. Clearly, a short term treatment regimen would be of major benefit to animal husbandrymen world wide. Furthermore, infected animals are a vector for the infection of humans using contaminated dairy products.

It is known that in vitro intraphagocytic killing of *Brucella abortus* in bovine mononuclear leukocytes was enhanced by multilamellar liposomes containing the aminoglycoside gentamicin. Dees, C., et al., "Enhanced Intraphagocytic Killing of *Brucella abortus* in Bovine Mononuclear Cells by Liposomes Containing Gentamicin", *Vet. Immunol. and Immunopath*, 8:171-182 (1985). In vitro killing of *Brucella abortus* was also enhanced when compared to free gentamicin. Other studies found that stable plurilamellar vesicle-entrapped aminoglycosides administered to *Brucella canis* infected mice and *Brucella abortus* infected guinea pigs effectively eliminated bacteria from the organs. Fountain, M. W., et al, "Treatment of *Brucella canis* and *Brucella abortus* in Vitro and in Vivo by Stable plurilamellar Vesicle-Encapsulated Aminoglycosides", *J. Inf. Dis.*, 152:529-535 (1985).

Recent studies found that a combination of a long-acting tetracycline such as oxytetracycline (e.g., LA-200 TM, Pfizer, Terra haute, IN) and streptomycin apparently cured 67% of infected dairy cows. Milward, F. W., "Effectiveness of Various Therapeutic Regimens for Bovine Brucellosis", *Am. J. Vet. Res.*, 45:1825-88 (1984); Nicoletti, P. W., "Efficacy of Long-Acting Oxytetracycline Alone or Combined with Streptomycin in the treatment of Brucellosis", *Vet. Med. Assoc*, 187:493-95 (1986). Other studies indicated that extension of treatment improved the cure rate to over 90%. However the treatment regimen required was both lengthy and laborious, requiring approximately one month maintainence of therapeutically effective levels of antibiotic in tissue. Therefore, attempts have been made to reduce the length and difficulty of treatment and increase the efficiency of the antibiotics employed.

Treatment of pathological mammary conditions has been beset with the problem of administering therapeutically effective levels of therapeutic agent into the mammary tissue with special reference to the lymphatic system serving the mammary gland, the proximal mammary lymph nodes. Infections and neoplasms of mammary tissue and proximal lymph nodes have proved resistant to treatment.

SUMMARY OF THE INVENTION

The instant invention presents a method of treating Brucella spp. infections in an animal, including humans, and particularly dairy animals, by administration of a therapeutically effective amount of aminoglycoside in liposome form by intramammary infusion. In a preferred embodiment the aminoglycoside is streptomycin, which is administered at a dosage of about 35 to about 50 mg/kg body weight.

An effective dosage regimen comprises administering the streptomycin in about 2 to about 5 doses.

The aminoglycoside is preferably administrable in conjunction with a therapeutically effective amount of a tetracycline, including long-acting oxytetracycline (e.g., oxytetracycline in a pyrrolidine carrier), particularly, as to oxytetracycline, at from about 10 to about 30 mg/kg body weight.

The liposome form preferred in this invention is stable plurilamellar vesicles, which in one embodiment comprise phosphatidylcholine.

In a particular embodiment the liposomes comprise at least about equal amounts of lipid and streptomycin sulfate (w/w).

This invention further includes a method of administering a therapeutic agent to a proximal mammary lymph node of an animal comprising intramammary infusion of the therapeutic agent in liposome form.

In various embodiments the therapeutic agent is an anti-infective agent or antineoplastic agent, and/or the liposomes are stable plurilamellar vesicles, and/or the liposomes comprise phosphatidylcholine.

Preferred anti-infective agents are imidazoles and β-lactams. Preferred antineoplastic agents are doxorubicin, cisplatin, and 5-fluorouracil.

BRIEF DESCRIPTION OF THE DRAWINGS

FIG. 2 graphically represents the effectiveness of a two stage treatment of *B. canis* infections in mice using SPLV-entrapped streptomycin based on *B. canis* recoverable from organs of infected mice.

FIG. 3 graphically represents the effectiveness of a two stage treatment of *Brucella abortus* in guinea pigs using SPLV-entrapped streptomycin.

DETAILED DESCRIPTION OF THE INVENTION

Figure 1:
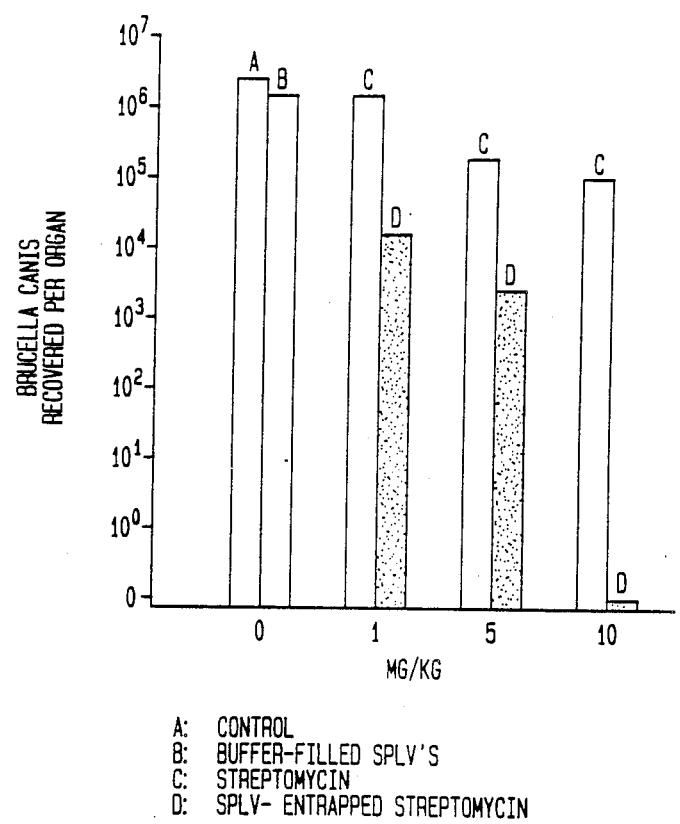
FIG. 1 graphically represents the effectiveness of a two stage treatment of *Brucella canis* infections in mice using SPLV-entrapped streptomycin based on *B. canis* recoverable from spleens of infected mice.

Liposomes are completely closed lipid bilayer membranes containing an entrapped aqueous volume. Liposomes may be unilamellar vesicles (possessing a single bilayer membrane) or multilameller vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "head" orient towards the aqueous phase.

The original liposome preparation of Bangham, et al. (J. Mol. Biol., 1965, 13:238–252) involves suspending phospholipids in an organic solvent which is then evaporated to dryness leaving a phospholipid film on the reaction vessel. Next, an appropriate amount of aqueous phase is added, the mixture is allowed to "swell," and the resulting liposomes which consist of multilamellar vesicles (MLVs) are dispersed by mechanical means. This technique provides the basis for the development of the small sonicated unilamellar vesicles described by Papahadjopoulos et al. (Biochim. Biophys, Acta., 1968, 135:624–638), and large unilamellar vesicles.

Unilamellar vesicles may be produced using an extrusion apparatus by a method described in Cullis et al., PCT application No. WO 86/00238, published Jan. 16, 1986, entitled "Extrusion Technique for Producing Unilamellar Vesicles" incorporated herein by reference. Vesicles made by this technique, called LUVETS, are extruded under pressure through a membrane filter.

Another class of liposomes are those characterized as having substantially equal intralamellar solute distribution. This class of liposomes is denominated as stable plurilamellar vesicles (SPLV) as defined in U.S. Pat. No. 4,522,803 to Lenk, et al., monophasic vesicles as described in U.S. Pat. No. 4,558,578 to Fountain, et al. and frozen and thawed multilamellar vesicles (FATMLV) wherein the vesicles are exposed to at least one freeze and thaw cycle; this procedure is described in Bally et al., PCT Publication No. 87/00043, Jan. 15, 1987, entitled "Multilamellar Liposomes Having Improved Trapping Efficiencies". The above noted references are incorporated herein by reference.

As used herein, liposome form will be understood to be an expansive term including, along with the above noted liposomes, lipid aggregates, lipid vesicles, and lipid-therapeutic agent complex.

A variety of sterols and their water soluble derivatives have been used to form liposomes; see specifically Janoff et al., PCT Publication No. WO 85/04578, published Oct. 24, 1985, entitled "Steroidal Liposomes." Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. WO 87/02219, published Apr. 23, 1987, entitled "Alpha Tocopherol-Based Vesicles", corresponding to U.S. Pat. No. 4,861,580, issued Aug. 29, 1989.

In the present invention, the term lipid as used herein shall mean any suitable material resulting in a bilayer such that a hydrophobic portion of the lipid material orients toward the interior of the bilayer while a hydrophilic portion orients toward the aqueous phase. Lipids further include highly hydrophobic compounds such as triglycerides, sterols such as cholesterol which can be incorporated into the bilayer. The lipids which can be used in the liposome formulations of the present invention are the phospholipids such as phosphatidylcholine (PC), phosphatidylethanolamine (PE), phosphatidylserine (PS), phosphatidylglycerol (PG), phosphatidic acid (PA), phosphatidylinositol (PI), sphingomyelin (SPM), and the like, alone or in combination. The phospholipids can be synthetic or derived from natural sources such as egg or soy. Useful synthetic phospholipids are dymyristoylphosphatidylcholine (DMPC) and dimyristoylphosphatidylglycerol (DMPG). The liposomes can also contain other steriod components such as polyethylene glycol derivatives of cholesterol (PEG-cholesterols), coprostanol, cholestanol, or cholestane, and combinations of PC and cholesterol. They may also contain organic acid derivatives of sterols such as cholesterol hemisuccinate (CHS), and the like. Organic acid derivatives of tocopherols may also be used as liposome-forming ingredients, such as alpha-tocopherol hemisuccinate (THS). Both CHS-and THS-containing liposomes and their tris salt forms may generally be prepared by any method known in the art for preparing liposomes containing these sterols. In particular, see the procedures of Janoff, et al., PCT Publication No. WO 85/04578, published Oct. 24, 1985, entitled "Steroidal Liposomes," and Janoff, et al., PCT Publication No. WO 87/02219, published Apr. 23, 1987, entitled "Alpha-Tocopherol Based Vesicles," filed Sept. 24, 1986, respectively. The liposomes may also contain glycolipids.

Virtually any bioactive compound can be entrapped within a SPLV (entrapped is defined as entrapment within the aqueous compartment or within the membrane bilayer). Such compounds include but are not limited to antibacterial compounds. When placed in a buffer containing isotonic saline at neutral pH, SPLVs containing antibiotic are stable for more than four months, as demonstrated in Table II. These data indicate that none of the antibiotic originally encapsulated within the SPLVs leaked out in the period of the experiment.

TREATMENT OF PATHOLOGIES

A number of pathological conditions which occur in man, animals and plants may be treated more effectively by encapsulating the appropriate compound or compounds in SPLVs. These pathologic conditions include but are not limited to infections (intracellular and extracellular), cysts, tumors and tumor cells, allergies, etc.

Many strategies are possible for using SPLVs in the treatment of such pathologies, a few overall schemes are outlined below which are particularly useful in that they take advantage of the fact that SPLVs when administered in vivo are internalized by macrophages.

In one scheme, SPLVs are used to deliver therapeutic agents to sites of intracellular infections. Certain diseases involve an infection of cells of the reticuloendothelical system, e.g., brucellosis. These intracellular infections are difficult to cure for a number of reasons: (1) because the infectious organisms reside within the cells of the reticuloendothelial system, they are sequestered from circulating therapeutic agents which cannot cross the cell membrane in therapeutically sufficient concentrations, and, therefore, are highly resistant to treatment (2) often the administration of toxic levels of therapeutic agents are required in order to combat such infections; and (3) the treatment has to be completely effective because any residual infection after treatment can reinfect the host organism or can be transmitted to other hosts.

According to one mode of the present invention, SPLVs containing an appropriate biologically active compound are administered (preferably intraperitoneally or intravenously) to the host organism or potential host organism (e.g., in animal herds, the uninfected animals as well as infected animals may be treated). Since phagocytic cells internalize SPLVs, the administration of an SPLV-encapsulated substance that is biologically active against the infecting organism will result in directing the bioactive substance to the site of infection. Thus, the method of the present invention may be used to eliminate infection caused by a variety of microorganisms, bacteria, parasites, fungi, mycoplasmas, and viruses, including but not limited to: Brucella spp., Mycobacterium spp., Salmonella spp., Listeria spp., Francisella spp., Histoplasma spp., Corynebacterium spp., Coccidiodes spp. and lymphocytic choriomeningitis virus.

The therapeutic agent selected will depend upon the organism causing the infection. For instance, bacterial infections may be eliminated by encapsulating an antibiotic. The antibiotic can be contained within the aqueous fluid of the SPLV and/or inserted into the vesicle bilayer. Suitable antibiotics include but are not limited to: penicillin, ampicillin, netacillin, carbencillin, tetracycline, tetracycline hydrochloride, oxtetracycline hydrochloride, chlortetracycline hydrochloride, 7-chloro-6-dimethyltetracycline, doxycycline monohydrate, methacycline hydrochloride, minocycline hydrochloride, rolitetracycline, dihydrostreptomycin, streptomycin, gentamicin, kanamycin, neomycin, erythromycin, carbomycin, oleandomycin, troleandomycin, Polymysin B collistin, cephalothin sodium, cephaloridine, cephaloglycin dehydrate, and cephalexin monohydrate.

We have demonstrated the effectiveness of such treatments in curing brucellosis (see Examples, infra). By the procedure of this invention, the effectiveness and duration of action are prolonged. It is surprising that this system is effective for treating infections which do not respond to known treatments such as antibiotics entrapped in MLVs. Successful treatment is unexpected since any small remaining infections will spread and the infectious cycle will commence again. We have also demonstrated success in treatment lymphocytic choriomeningitis virus infection.

Of course, the invention is not limited to treatment of intracellular infections. The SPLVs can be directed to a variety of sites of infection whether intracellular or extracellular. For instance, in another embodiment of the present invention, macrophages are used to carry an active agent to the site of a systemic extracellular infection. According to this scheme, SPLVs are used to deliver a therapeutic substance to uninfected macrophages by administering the SPLVs in vivo (preferably intraperitoneally or intravenously). The macrophages will coalesce with the SPLVs and then become "loaded" with the therapeutic substance; in general, the macrophages will retain the substance for approximately 3 to 5 days. Once the "loaded" macrophages reach the site of infection, the pathogen will be internalized by the macrophages. As a result, the pathogen will contact the therapeutic substance contained within the macrophage, and be destroyed. This embodiment of the invention is particularly useful in the treatment of Staphylococcus aureus mastitis in man and cattle.

If the site of infection or affliction is external or accessible the SPLV-entrapped therapeutic agent can be applied topically. A particularly useful application involves the treatment of eye afflictions. In the case of ocular afflictions, SPLVs containing one or more appropriate active ingredients may be applied topically to the afflicted eye. A number of organisms cause eye infections in animals and man. Such organisms include but are not limited to: Moraxella spp., Costridium spp., Corynebacterium spp., Diplococcus spp., Flavobacterium spp., Hemophilus spp., Klebsiella spp., Leptospira spp., Mycobacterium spp., Neisseria spp., Propionibacterium spp., Proteus spp., Pesudomonas spp., Serratia spp., Escherichia spp., Staphylococcus spp., Streptococcus spp. and bacteria-like organisms including Mycoplasma spp. and Rickettsia spp. These infections are difficult to eliminate using conventional methods because any residual infection remaining after treatment can reinfect through lacrimal secretions.

Aminoglycoside will be understood to mean aminoglycosides and analogues and derivatives thereof, including streptomycin, dihydrostreptomycin, tobramycin, neomycin B, paromycin, ribostamycin, lividomycin, kanamycin A and B, viomycin, gentamicin (including $C_1$, $C_{1a}$, and $C_2$), sisomicin, netilimicin and amikacin.

Tetracycline will be understood to mean terracyclines and analogues and derivatives thereof, including oxytetracycline, chlortetracycline, doxycycline, demeclocycline, methacycline, and minocycline.

Antineoplastic agents will be understood to include vinca alkaloids (e.g., vincristine, vinblastine), epipodophyllotoxins (e.g., etoposide, teniposide), antibiotics (e.g., dactinomycin, daunomycin, doxorubicin, bleomycin, mithramycin, mitomycin), enzymes (e.g., L-asparaginase), platinum coordinated complexes (e.g., cisplatin), substituted urea (e.g., hydroxyurea), methylhydrazine derivatives (e.g., N-methylhydrazine,MIH), adrenocortical supressants (e.g., aminoglutethimide), nitrogen mustards (e.g., mechlorethamine, cyclophosphamide, L-sarcolysin, uracil mustard, chlorambucil), alkyl sulfonates (e.g., busulfan), nitrosoureas (e.g., carmustine, lomustine, semustine, streptozocin), triazines (e.g., dimethyltriazenoimidazolecarboxamide), folic acid analogues (e.g., amethopterin), pyrimidine analogues (e.g., 5-flurouracil, cytosine arabinoside), purine analogues (e.g., 6-mercaptopurine, 6-thioguanine) and hormones and antagonists (e.g., prednisone, hydroxyprogesterone, medroxyprogesterone acetate, megestrol acetate, diethylstilbesterol, ethinyl estradiol, tamoxifen, testosterone propionate, fluoxymesterone).

"Therapeutic agents" shall be understood to include biologically active agents ("bioactive agents") as well as other medically useful agents such as contrast materials (e.g., dyes) and diagnostic materials.

Depending upon the purpose of delivery, the SPLVs may be administered by a number of routes: in man and animals this includes but is not limited to injection (e.g., intravenous, intraperitoneal, intramuscular, subcutaneous, intraauricular, intramammary, intraurethrally, etc.), topical application (e.g., on afflicted areas), and by absorption through epithelial or mucocutaneous linings (e.g., ocular epithelia, oral mucosa, rectal and vaginal epithelial linings, the respiratory tract linings, nasopharyngeal mucosa, intestinal mucosa, etc.); in plants and protists this includes but is not limited to direct application or organism, dispersion in the organism's habitat, addition to the surrounding environment or surrounding water, etc.

The therapeutic agent selected will depend upon the organism causing the infection. For instance, bacterial infections may be eliminated by encapsulating an antibiotic. The antibiotic can be contained within the aqueous fluid of the SPLV and/or instead into the vesicle bilayer. Suitable antibiotics include tetracycline, tetracycline hydrochloride, oxytetracycline hydrochloride, dihydrostreptomycin, streptomycin, gentamicin, kanamycin, neomycin, erythromycin, carbomycin, oleandomycin, troleandomycin, polymixin B collistin, cephalothin sodium, cephaloridine, cephaloglycin dihydrate, and cephalexin monohydrate.

We have demonstrated the effectiveness of such treatments in curing brucellosis (see Examples, infra). By the procedure of this invention, the effectiveness and duration of action are prolonged.

In a series of experiments (Table I) involving 28 cows, it was determined that the administration of liposomal aminoglycoside was an effective treatment for brucellosis in animals. Eight of the treated cows were cured of brucellosis. All of the cows thus cured received an aminoglycoside (streptomycin) in liposome form. While previously reported work required about 12 doses of therapeutic agent, in the instant method in particular cases less than 12 doses and, in the preferred embodiments (including the intramammary infusion of liposomal aminoglycoside), as few as 2 intramammary doses and 2 adjunct doses. Further more in the most preferred method, the 4 doses were of the more easily administered type; two intramammary doses of liposome aminoglycoside and two intramuscular doses of long-acting oxytetracycline.

The intramammary doses stated are for cows but are easily translatable to other animals relative to the size of the animal. For streptomycin a dosage of about 20 to about 75 mg/kg may be used with about 35 to about 50 mg/kg prefered. For various animals and therapeutic agents the relative size of the animal is considered. Adult cows, depending on breed, are from about 800 to about 1500 pounds, adult sheep are from about 75 to 150 pounds and adult goats are from about 50 to 100 pounds. Intramammary doses for such animals will be generally adjusted relative to the body weight of the animal as compared the size of a cow. Thus goats will require a dose roughly about ⅕ to 1/30 of that of a cow and sheep roughly about 1/7 to 1/20. Similar adjustments are required for other animals such as camels, reindeer, water buffalo, and horses. So saying, however, a further adjustment of intramammary dose may be required to account for the relative size of the udder. In situations in which exact dosages are required, a biopsy of mammary tissue or proximal mammary lymph node may be performed to ascertain the level of therapeutic agent present. The relative doses will be understood by those skilled in the art to be similar in relation to other therapeutic agents as compared in dosage to a dosage for cattle.

"Intramammary infusion" shall be understood to mean introducing material into the mammary tissue of an animal, primarily into the teat cistern and the associated afferent lymphatic system. This is done conveniently by way of the teat canal, but other methods of introduction such as injection into mammary tissue are similarly comtemplated. Administration may be to one or all teats of an animal. For clarity, reference to numbers of treatments or administrations does not refer to the number of teats treated but to the number of instances of treatment of the animal.

Proximal mammary lymph nodes will be understood to mean those lymph nodes within the mammary gland and those which receive lymph from the mammary gland.

In a liposome-drug delivery system, a therapeutic agent such as a drug is entrapped in or associated with the liposome and then administered to the patient to be treated. For example, see Rahman et al., U.S. Pat. No. 3,993,754; Sears, U.S. Pat. No. 4,145,410; Paphadjopoulos et al., U.S. Pat. No. 4,235,871; Schneider, U.S. Pat. No. 4,114,179; Lenk et al., U.S. Pat. No. 4,522,803; and Fountain et al., U.S. Pat. No. 4,588,578.

The mode of administration of the preparation may determine the sites and cells in the organism to which the compound will be delivered. Liposomes can be administered alone but will generally be administered in admixture with a pharmaceutical carrier selected with regard to the intended route of administration and standard pharmaceutical practice. The preparations may be injected parenterally, for example, intraperitoneally, intra-arterially or intravenously. The preparations may also be administered via oral, subcutaneous, intramuscular and, of course, intramammary routes. For parenteral administration, they can be used, for example, in the form of a sterile aqueous solution which may contain other solutes, for example, enough salts or glucose to make the solution isotonic. Other uses, depending upon the particular properties of the preparation, may be envisioned by those skilled in the art.

For administration to animals including humans in the curative treatment of disease states, the prescribing medical professional will ultimately determine the appropriate dosage for a given subject, and this can be expected to vary according to the age, weight, and response of the animal as well as the nature and severity of the disease. The dosage of therapeutic agent in liposomal form will generally be about that employed for the free therapeutic agent. In some cases, however, it may be necessary to administer doses outside these limits.

Aminoglycoside in liposome form will cure *Brucella abortus*. However, especially with large dairy animals, some methods of drug administration such as intraperitoneal and intravenous are impractical, costly and (due the unruliness of the animals) potentially dangerous to the individual administering the treatment. Intramammary infusion is a far simpler method by which to administer therapeutic agent. Equipment already available in the art may be utilized to insert therapeutic agent through the teat canal. Further and unlike intraperitoneal administration, clean but not sterile conditions are usually suitable for intramammary administration.

As presented here, intramammary infusion of aminoglycoside in liposome form is an effective method to treat livestock infected with *Brucella abortus*.

This treatment may be effective in as few as about two to five applications. In the preferred embodiment it is supplemented with co-administration of long-acting oxytetracycline, usually at about 10 to 30 mg/kg animal weight and preferably about 20 mg/kg.

In one embodiment stable plurilamellar vesicles (SPLV) are the liposomes used but other types of liposomes are also contemplated. SPLV's of phosphatidylcholine are of particular use in this invention.

The treatment via intramammary infusion of liposomes additionally permits the treatment of the mammary tissue and proximal mammary lymph nodes of an animal for other medical conditions. This treatement is essentially perfusion (or retrograde perfusion) of the lymph system. Liposome forms may be administered to the lymph system directly as in intramammary infusion, or indirectly such as by subcutaneous or intraperitonal administration of liposome forms that will then collect in the lymph nodes. For mammary glands administration is accomplished in a fashion similar to brucellosis treatment by incorporating at least one therapeutic agent such as an antibacterial agent, antiviral agent, antiparasitic agent, or antifungal agent (collectively "anti-infective agent") antineoplastic agents or other therapeutic agent into a liposome form and administering such liposome form alone or in combination with additional therapeutic agents to an animal. Tests of this method with the dye Texas red indicate that liposomes introduced into the teat cistern perfuse the mammary tissue and congregate in the proximal lymph nodes in about 24 hours. Anti-infectives such as imidazoles, aminoglycosides and $\beta$-lactams, as well as antineoplastics are useful in such method. Dosage will be similar to the dosage of free drug given in a localized manner.

Imidazole will be understood to refer to imidazoles including, without limitation, miconazole, terconazole, biconazole, ketaconazole, econazole, clotrimazole and metronidazole as well as analogs and derivatives thereof characterized in having anti-infective properties.

$\beta$-lactams will be understood to refer to synthetic, semisynthetic and natural penicillins, cephalosporins, monobactams, and thinamycins, such as oxacillin, cephapirin, aztreonam and imipenem.

Preparation and testing of materials of the invention are described below.

LIPOSOMES

The aminoglycoside liposomes were prepared as streptomycin sulfate containing liposomes. One process used employed egg phosphatidylcholine to make SPLVs, while another was the "emulsion-inversion process though other methods of liposome preparation will also be suitable.

The emulsion inversion process comprised creating a water-in-oil emulsion wherein the aqueous solution consisted of, in the case of streptomycin sulfate, 480 mg/ml of streptomycin sulfate in normal saline and the oil consisted of a lipid, here dried phosphatidylcholine (lecithin). In the preferred process small (about 100 ml) aliquots of the aqueous solution were added to about 500 gm of lecithin and blended until thoroughly mixed. The process requires that in the first such aqueous addition the total quantity of water added to the lipid phase be insufficient to fully hydrate the lipid—thus yielding the water-in-oil emulsion. As successive aliquots of aqueous phase are added the amount of water available exceeds that amount necessary to fully hydrate the lipid and the mixture inverts into an oil-in-water emulsion. At this point the hydrated lipids have become liposomes. Since encapsulation of therapeutic agent—here streptomycin—occurs prior to full hydration therapeutic agent was added only for the pre-full hydration additions of aqueous solution. In this example this was the first three aqueous additions. Of course the nature of the particular lipid as well as its state of dehydration will vary the amounts of aqueous phase for the pre-and post-hydration stages. The exact proportions will be clear to those skilled in the art as delineated by the stage of hydration at which liposomes appear.

The resulting liposomes were suspended in 0.9% saline. In some cases, the liposomes were reduced in size by passing them through a 0.5 micron orifice under pressure. The total and entrapped streptomycin content was determined by high performance liquid chromatographic procedure (Wall, T. J., "Determination of Streptomycin Sulfate by High Performance Liquid Chromatography", *J Chromatography*, 219:89-100, (1981)) or an agar-well diffusion assay using Antibiotic Assay Medium #5 (BBL; Baltimore, Md.) and *Bacillus subtilis* (ATCC #6633) as an indicator organism. The particular assay method is not critical and other methods will be known to those skilled in the art.

The total phospholipid phosphate was determined using a modified Bartlett's assay (Rouser, G., et al., Lipids 5:494, 1970).

Lipid composition was qualtitatively assessed by thin layer chromatography. Vesicle size was estimated using a Nicomp (Hiac/Royco; Goleta Calif.) Model 270 submicron particle sizes for vesicles less than 1 micron in diameter and either a Brinkman (Brinkman Instruments, Westbury, N.Y.) Particle Size analyzer or a Malvern (Malvern Instruments, Malvern England) Particle Sizer for vesicles in the range of 1-30 microns diameter.

The liposomes produced by either SPLV or emulsion-inversion entrapped about 26 to 80% of the aminoglycoside present. The exogenous aminoglycoside can be washed free of the liposomes but was not in the examples reported here.

BACTERIOLOGICAL STUDIES

Pre-treatment cultures of udder secretions were made to confirm shedding of *Brucella abortus* by subject animals. Samples for culture were collected every 3 to 4 days during therapy and for 3 to 6 weeks after the last treatment. Cows were slaughtered and the selected tissues (the supramammary, iliac and head lymph nodes and the udders) were collected, processed in a tissue homogenizer and plated.

All samples were plated on trypose agar containing crystal violet and incubated at 37° C. with 5% $CO_2$ for 5 to 7 days.

Animals from which Brucella could no longer be recovered from udder secretions nor from any tissues examined at necropsy were considered cured.

TREATMENT PROTOCOLS

The treatment of the test animals employed, in various combinations, 4 techniques:

(1) intraperitoneal injection of aminoglycoside liposomes;

(2) intravenous injection of aminoglycoside liposomes;

(3) intramammary infusion of aminoglycoside liposomes; and (4) intramuscular injection of a tetracycline.

Intraperitoneal (IP) injections of streptomycin sulfate in liposome form utilizing liposomes with either 59 mg/kg to 118 mg/kg animal weight of therapeutic agent were administered per dose in a volume of approximately 360 ml at 3–4 day intervals.

Intravenous injections of aminoglycoside in liposome form were administered at 20 mg/kg animal weight in a volume of 180 to 400 ml per dose at 3 day intervals. Intervals of from about 1 to 5 days are also acceptable.

Intramammary infusion utilized 50 ml of aminoglycoside in liposome form per udder quarter at 1-3 day intervals. Intervals up to about 5 days are also acceptable. Infusion was accomplished by inserting a teat cannula in the teat canal and injecting the liposome preparation through a bunt needle into the teat cistern.

Intramuscular injection of tetracycline employed oxytetracycline in a pyrrolidine vehicle (LA-200 TM) which will be referred to as long-acting oxytetracycline. Long-acting oxytetracycline was used in a solution of 200 mg/ml administered intramuscularly in the cervical region at a dosage of 20 mg/kg animal weight injecting 10–15 ml per cite at 3 to 4 day intervals. Intervals of from about 1 to 6 days are also acceptable.

EXAMPLE 1
TABLE I(A), INTRAMAMMARY AND INTRAPERITONEAL

Two cows naturally infected with Brucella abortus were used. The first cow weighed 500 kg and received intraperitoneal streptomycin sulfate in liposome form (emulsion-inversion liposomes) in 2 treatments spaced 3 days apart of 325 ml of liposomes, and a dosage of 59 mg/kg with the total streptomycin administered intraperitoneally being 60 gm. This cow also received 4 intramammary infusions of streptomycin sulfate in liposome form.

These intramammary infusions were into udder quarters previously determined to be shedding Brucella. The 4 intramammary infusions were each of 3.75 gm of streptomycin sulfate in 50 ml of liposome and totalled 15 gms. These 4 infusions where at 2 to 3 day intervals.

The second cow weighed 420 kg and also received 59 mg/kg animal weight intraperitoneal streptomycin sulfate in liposome form in 2 treatments each in a volume of 270 ml at 3 day intervals for a total of 50 gms streptomycin sulfate. This cow was determined to be shedding from two udder quarters and received an intramammary infusion into each quarter of 7.5 gm of liposome form streptomycin sulfate each quarter receiving 50 ml volumes of liposomes. This cow received therapeutic agent only in the 2 positive quarters for 3 of the 4 doses administered, and one administration to all 4 quarters. Total intramammary administration was 76 gms of streptomycin sulfate in liposome form.

Both cows were cured in 6 total treatments by the combined use of intraperitoneal aminoglycoside liposomes and intramammary infusion of aminoglycoside liposomes.

EXAMPLE 2

TABLE I(B), INTRAPERITONEAL, INTRAMUSCULAR

Two cows determined to be shedding *Brucella abortus* were utilized. The first weighed 600 kg and received intraperitoneal streptomycin sulfate in liposome form (emulsion-inversion liposomes) in 5 treatments each of 385 ml of liposomes at 3 to 4 day intervals and a dosage of 59 mg/kg with total streptomycin administered intraperitoneally being 177 gms. This cow also received 5 treatments of long-acting oxytetracycline intramuscularly in doses of 20 mg/kg at 3 to 4 day intervals.

In similar fashion a second cow of 490 kg received 5 doses of intraperitoneal streptomycin sulfate in liposome form (emulsion-inversion liposomes) in volumes of 315 ml per dose at 3 to 4 day intervals. Dosage was at 50 mg/kg for a total of 145 gm total streptomycin. Five doses of long-acting oxytetracycline were also administered intramuscularly at 20 mg/kg each dose in 3 to 4 day intervals.

In 10 doses (none of which were the more easily administered intramammary infusion) both animals were cured.

EXAMPLE 3

TABLE I(C), INTRAVENOUS, INTRAMUSCULAR

Two cows determined to be shedding *Brucella abortus* were utilized. The first cow weighed 580 kg and received 2 intravenous doses of streptomycin sulfate of 400 ml in liposome form (SPLV liposomes) in 3 day intervals. Dosage was at 75 mg/kg for at total of 86 gms. This animal also received intramuscular long-acting oxytetracycline at 20 mg/kg in two doses at 3-4 day intervals. This animal was cured.

The second cow weighed 580 kg received exactly the same treatment and was not cured.

EXAMPLE 4

TABLE I(D), INTRAMAMMARY, INTRAMUSCULAR

This example utilized 5 cows two of which were cured. Due to the ease of treatment utilizing the relatively simple intramammary infusion of liposome form (SPLV liposomes) aminoglycoside supplemented with long-acting oxytetracycline this is the preferred method.

All five cows received two intramuscular doses of long acting oxytetracycline at 20 mg/kg in 3 to 4 day intervals.

Two cows received 2 treatments at 3 day intervals of 5.4 gm of streptomycin sulfate by intramammary infusion into each quarter of the udder in 50 ml of liposomes for a total of 43 gms of streptomycin. One of these cows was cured in the 4 treatments. Three cows received the same treatment except that 3.5 gm of streptomycin sulfate liposomes were used in each udder quarter for a total of 28 gms. One of the three cows was cured in the 2 intramammary treatments accompanied by the 2 intramuscular treatments.

EXAMPLE 5

TABLE I(E), INTRAPERITONEAL

Six cows weighing from 396 to 508 kg shedding *Brucella abortus* were used. Each cow received 5 intraperitoneal doses of streptomycin sulfate in liposome form (4 receiving emulsion-inversion liposomes and 2 receiving SPLV liposomes) in 1 to 3 day intervals and no other treatment.

Streptomycin sulfate was administered to 2 cows at 59 gm/kg, 2 cows at 62 mg/kg and 2 cows at 118 mg/kg. One cow, weighing 403 kg receiving 5 doses 62 mg/kg in 330 ml in liposome form (SPLV) for a total of 123 gms of streptomycin, was cured.

EXAMPLE 6

TABLE I(F), INTRAVENOUS

Two cows shedding *Brucella abortus* were used. Each cow weighed 580 kg and received streptomycin sulfate in liposome form in 2 doses of 1 to 3 day intervals. Dosage was at 75 mg/kg and 400 ml in liposome form (SPLV liposomes) was used each dose. Total streptomycin sulfate administered was 86 gms with no cure.

EXAMPLE 7

TABLE I(G), INTRAVENOUS, INTRAMAMMARY

Three cows shedding *Brucella abortus* were used. Each cow weighed 625 kg and each received two doses of 20 mg/kg and each received two doses of 20 mg/kg streptomycin sulfate in liposome form (SPLV liposomes) at 1 to 3 day intervals for a total of 25 gms of streptomycin sulfate. Each dose was 180 ml of liposome. Each cow also received 2 treatments of streptomycin sulfate in liposome form at 3.5 gms per udder quarter, 50 ml of liposome, per treatment for a total of 28 gms. No cows were cured.

EXAMPLE 8

TABLE I(H), INTRAMAMMARY

Six cows shedding *Brucella abortus* were used. Three cows received a single treatment of streptomycin sulfate in liposome form (SPLV liposomes). Treatment was to two of the udder quarters on each cow in 50 ml volumes of liposomes. One cow received 0.96 gms per udder quarter treated, one received 1.93 gms per udder quarter treated, and one received 3.85 gms per udder quarter treated.

Of the other three cows, one received two doses by intramammary infusion of streptomycin sulfate in 50 ml in liposome form (SPLV liposomes), each treatment being 0.96 gm streptomycin sulfate per udder quarter to all 4 quarters. Doses were at an interval of 3 days. One received 4 doses by intramammary infusion of streptomycin sulfate in 50 ml in liposome form, each treatment being 1.93 gm streptomycin sulfate per udder quarter to all 4 quarters at an interval of 3 days. On receiving 2 doses by intramammary infusion of streptomycin sulfate in 50 ml in liposome form, each treatment being 3.85 gm streptomycin sulfate per udder quarter to all 4 quarters at an interval of 3 days. No animals were cured.

EXAMPLE 9

SPLVS CONTAINING ANTIBIOTICS

A 5 ml diethyl ether solution of 100 mg lecithin ws prepared. The mixture was placed in a round-bottom flask. Then a solution (0.3 ml) containing 100 mg of streptomycin sulfate at pH 7.4 in 5 mM HEPES (4-[2-Hydroxyethyl]piperazino 2-ethane sulfonic acid)/0.0725M NaCl/0.0725M KCl was pipetted into the glass vessel containing the diethyl ether solution of lipid. The mixture was placed in a bath sonicator (Laboratory Supplies Co., Inc.) type 10536 for several minutes, (80 kHz frequency:output 80 watts) while being dried to a viscous paste by passing thereover a gentle stream of nitrogen.

To the viscous paste remaining was added 10 ml of 5 mM HEPES. The resulting SPLV preparation, containing streptomycin, was suspended in the buffer solution, shaken for several minutes on a vortex mixer, and freed of non-encapsulated streptomycin by centrifuging at 12,000×g for 10 minutes at 20° C. The resulting cake was suspended in 0.5 ml of 5 mM HEPES.

The procedure described above was followed except that streptomycin was substituted by each one of the following: dihydrostreptomycin, gentamycin sulfate, ampicillin, tetracycline hydrochloride, and kanamycin.

EXAMPLE 10

SPLV Mediated Delivery In Vitro

In the following example, SPLV mediated delivery of antibiotics to macrophages in culture was demonstrated.

Peritoneal macrophages were obtained by peritoneal lavage from $C_{57}BLK$ adult male mice and suspended in minimal essential medium (M.E.M.) pH 7.2 containing 10% heat-inactivated fetal calf serum. Cells were suspended at a concentration of $1 \times 10^6$ cells per ml in 96-well tissue culture dishes. To cultures containing adherent peritoneal macrophages, were added *B. canis* at concentrations of $1 \times 10^6$CFU (colony forming units) per ml. After 12 hours, bacteria not engulfed by peritoneal macrophages were removed by repeated washings with M.E.M. After washing of peritoneal macrophage cultures, they were divided into 5 groups, each containing 12 replicate cultures per group. Group 1, designated Controls, received no treatment. Group 2 received aqueous streptomycin sulfate at a concentration of 1 mg/ml. Group 3 received buffer-filled SPLVs. Group 4 received aqueous streptomycin sulfate (1 mg/ml) plus preformed buffer-filled SPLVs. Group 5 received SPLVs containing streptomycin sulfate (1 mg/ml). After 24 hours, supernatants were removed by repeated washings and peritoneal macrophages were disrupted by repeated freezing and thawing. Serial dilutions of disrupted macrophages were plated onto brucella agar and, after 4 days, surviving *B. canis* were determined by limiting dilution techniques. Results shown in Table VIII indicate that SPLV-entrapped streptomycin was totally effective in killing and eliminating the intracellular *B. canis* infection in vitro.

The experiment was repeated with *B. abortus* exactly as described above except that peritoneal macrophages were obtained by peritoneal lavage from adult female albino guinea pigs. Results are also shown in Table VIII.

EXAMPLE 11

Treatment Intracellular Infections

The following examples demonstrate how SPLVs can be used in treating intracellular infections. The data presented demonstrates: (1) the effectiveness of using antibiotics encapsulated in SPLVs in the treatment of disease and (2) the greater efficiency which is obtained by administering multiple doses of the SPLV preparation.

Brucellosis causes worldwide economic and public health problems. Brucellosis is caused by Brucella spp. It is adapted to many mammalian species, including man, domestic animals and a variety of wild animals. Six Brucella spp. cause brucellosis in animals; they are *B. abortus, B. canis, B. melitensis, B. neotomae, B. ovis* and *B. suis*. Both domestic and wild animals serve as reservoirs for potential spread of brucellosis to other animals and man.

Such infections cannot be cleared with antibiotics because the infectious organisms reside within the cells of the reticuloendothelial system and are highly resistant to bactericidal activities of antibiotics. The quantity of antibiotics required and the length of treatment results in either toxic effects on the animal or an unacceptable high concentration of the antibiotic in the tissues of the animal. The further difficulty in treating this disease is that the treatment has to be completely effective since any remaining infection will simply spread and the cycle commences once again. The economic impact of such diseases is demonstrated by the millions of dollars of valuable cattle which are lost each year due to spontaneous abortion. The only potential way to combat such infectious outbreaks is to quarantine and then slaughter the animals.

The examples which follow comprise incorporating an antibiotic into SPLVs, and then administering the encapsulated active substance to the animals by inoculating the infected animals intraperitoneally.

Effect of a Single Treatment of *B. Canis* Infection Using SPLV-Entrapped Antibiotic Eighty adult male Swiss mice were infected intraperitoneally (O.P.) with *B. canis* ATCC 23365 ($1 \times 10^7$CFU) and divided into 8 groups of 10 mice each. Seven days post-inoculation with *B. canis* groups were treated as follows: Group 1, designated Controls, received no treatment; Group 2 received buffer-filled SPLVs (0.2 ml I.P.); Group 3 received aqueous streptomycin sulfate (1 mg/kg body weight in a total administration of 0.2 ml I.P.); Group 4 received aqueous streptomycin sulfate (5 mg/kg body weight) in a total administration of 0.2 ml I.P.; Group 5 received aqueous streptomycin sulfate (10 mg/kg body weight) in a total administration of 0.2 ml I.P.; Group 6 received SPLVs containing streptomycin sulfate (1 mg/kg body weight) in a total administration of 0.2 ml I.P.; Group 7 received SPLVs containing streptomycin sulfate (5 mg/kg body weight) in a total administration of 0.2 ml I.P.; and Group 8 received SPLVs containing streptomycin sulfate (10 mg/kg body weight) in a total administration of 0.2 ml I.P. On day 14 post-inoculation with *B. canis*, all animals were sacrificed and spleens were removed aseptically. Spleens were homogenized and serially diluted onto brucella agar to determine the number of surviving *B. canis* in spleens after treatment. Results after 4 days incubation are shown in Table IV.

EXAMPLE 12

Effect of Multiple Treatment of *B. Canis* Infection Using SPLV-Entrapped Antibiotic Eighty adult male Swiss mice were infected with *B. canis* ATCC 23365 ($1 \times 10^7$CFU, I.P.) and divided into 8 groups of 10 mice each. Seven and 10 days post-inoculation with *B. canis* groups were treated as follows: Group 1, designated Controls, received no treatment; Group 2 received buffer-filled SPLVs (0.2 ml I.P.); Group 3 received aqueous streptomycin sulfate (1 mg/kg body weight in a total administration of 0.2 ml I.P.); Group 4 received aqueous streptomycin sulfate (5 mg/kg body weight) in a total administration of 0.2 ml I.P.; Group 5 received aqueous streptomycin sulfate (10 mg/kg body weight) in a total administration of 0.2 ml I.P.; Group 6 received SPLVs containing streptomycin sulfate (1 mg/kg body weight) in a total administration of 0.2 ml I.P.; Group 7 received SPLVs containing streptomycin sulfate (5 mg/kg body weight) in a total administration of 0.2 ml I.P.; and Group 8 received SPLVs containing streptomycin sulfate (10 mg/kg body weight) in a total administration of 0.2 ml I.P. On day 14 post-inoculation with *B. canis*, all animals were sacrificed and spleens were removed aseptically. Spleens were homogenized and serially diluted onto brucella agar to determine the number of surviving *B. canis* in spleens after treatment. Results after 4 days incubation are shown in FIG. 1.

The results of various two-stage treatment regimens on *B. canis* infections in vivo presented in FIG. 3, demonstrate that in groups receiving aqueous streptomycin 7 and 10 days post-inoculation, very little reduction in surviving *B. canis* in spleens was observed. Only in groups receiving SPLV-entrapped streptomycin at a concentration of 10 mg/kg body weight administered on day 7 and 10 post-inoculation were all viable bacterial eliminated from spleens of infected animals.

In addition to the experiment described above, various tissues from *B. canis* infected mice after two treatments with SPLV-entrapped streptomycin were sampled as follows:

Thirty adult male Swiss mice were inoculated with *B. canis* ATCC 23365 ($1\times10^7$CFU, I.P.). Seven days post-inoculation animals were divided into 3 groups of 10 mice each. Group 1, designated controls, received no treatment; Group 2 received (on days 7 and 10 post-inoculation) aqueous streptomycin sulfate (10 mg/kg body weight) in each administration of 0.2 ml), I.P.; Group 3 received (on days 7 and 10 post-inoculation) SPLVs containing streptomycin sulfate (10 mg/kg body weight) in each administration of 0.2 ml, I.P. On days 14 to 75 post-inoculation with *B. canis* all animals were sacrificed and the following organs removed aseptically, homogenized and serially diluted onto brucella agar for isolation of *B. canis*: heart, lungs, spleen, liver, kidneys, testes. After 4 days incubation, results of surviving *B. canis* per organ are shown in FIG. 2.

Results of samplings of various tissues in *B. canis* infected mice after two treatment regimens with streptomycin presented in FIG. 2 demonstrated that in animals treated with SPLV-entrapped streptomycin, all tissues sampled from 14 to 75 days post-inoculation with *B. canis* were totally free to any viable *B. canis* organisms. In animals untreated or treated with aqueous streptomycin in concentrations and administration schedules identical to those receiving SPLV-entrapped streptomycin, viable *B. canis* organisms could be isolated in all tissues sampled from 14 to 75 days post-inoculation with *B. canis*.

EXAMPLE 13

Effect of Various SPLV-Entrapped Antibiotics on Treatment of Infection

Fifty adult male Swiss mice were inoculated with *B. canis* ATCC 23365 ($1\times10^7$CFU, I.P.). Seven days post-inoculation animals were divided into 10 groups of 5 mice each. Group 1, designated controls, received no treatment; Group 2 received buffer-filled SPLVs (0.2 ml, i.P.) on days 7 and 10 post-inoculation; Groups 3, 4, 5 and 6 received aqueous injections (0.2 ml I.P.) of dihydrostreptomycin, gentamicin, kanamycin or streptomycin 10 mg/kg body weight, I.P. on days 7 and 10 post-inoculation (N.B. Each of these antibiotics have been shown to kill *B. canis* in vitro).

Groups 7, 8, 9 and 10 received SPLVs containing dihydrostreptomycin, gentamicin, kanamycin, or streptomycin at 10 mg/kg body weight on days 7 and 10 post-inoculation. On day 14 post-inoculation with *B. canis*, all animals were sacrificed and spleens were removed aseptically, homogenized and serially diluted onto brucella agar for at isolation of *B. canis*. Results of surviving *B. canis* per organ after 4 days incubation are as shown in Table V.

The results from tests of various antibiotics on *B. canis* infected mice presented in Table V demonstrate that antibiotics which are effective in killing *B. canis* in vitro (i.e., in suspension culture) are also only effective in killing *B. canis* infections in vivo when they are encapsulated within SPLVs. Animals receiving either aqueous antibiotics, buffer-filled SPLVs or no treatment were in no case cleared of surviving *B. canis* in isolated spleen tissues.

EXAMPLE 14

Treatment of Dogs Infected with *B. canis*

Adult female beagles were inoculated with *B. canis* ATCC 23365 ($1 \times 10^7$ CFU) orally and vaginally. Seven days post-inoculation dogs were divided into 3 groups. Group 1, designated control, received no treatment; Group 2 received (on days 7 and 10 post-inoculation) aqueous streptomycin sulfate at 10 mg/kg body weight (each administration was 5.0 ml, I.P.). Group 3 received (on days 7 and 10 post-inoculation) SPLVs containing streptomycin sulfate at 10 mg/kg body weight (each administration was 3.0 ml, I.P.). Vaginal swabbings of dogs and heparinized blood samples were collected at regular intervals before, during, and at the termination of the study. These were cultured on brucella agar in order to isolate *B. canis*. Results are shown in Table VI. Serum samples were collected before, during, and at the termination of the study for determinations of serum antibody against *B. canis*. These results are also shown in Table VI. Twenty-one days post-inoculation with *B. canis*, all animals were euthanized. The following tissues were removed aseptically, homogenized and serially diluted onto brucella agar for isolation of *B. canis*: heparinized blood, vaginal exudate, lungs, spleen, synovial fluid, uterus, ovary, popliteal lymph nodes, salivary glands, tonsils, mediastinal lymph nodes, mesenteric lymph nodes, bone marrow, superficial cervical lymph nodes, and auxiliary lymph nodes. Results of surviving *B. canis* per tissue after 4 days incubation are shown in Table VII.

Results of culture and serological tests of dogs infected with *B. canis* before, during, and after two-stage antibiotic administration are presented in Table VI. All animals were serologically negative for previous exposure to *B. canis* as measured by negative serum titers, and were culture negative from blood cultures and cultures of vaginal swabbings. All animals were noted to be culture positive for both blood and vaginal cultures prior to treatments on days 7 and 10. Dogs treated with aqueous streptomycin or dogs receiving no treatment remained culture positive for bood and vaginal cultures during post-treatment periods prior to termination on day 21. Group 3, which received liposomes containing streptomycin, became culture negative one day after the first treatment and remained negative throughout post-treatment period. Dogs which received no treatment or aqueous streptomycin developed detectable serum titers against *B. canis* antigens by day 21 post-inoculation, while those treated with SPLVs containing antibiotics on days 7 and 10 post-inoculation did not develop any detectable antibody to *B. canis* antigen.

Results from isolation of *B. canis* from infected dogs treated with two-stage antibiotic administration which are presented in Table VII demonstrate that in dogs, only treatment with SPLVs containing streptomycin was effective in eliminating any viable *B. canis* in all tissues from all organ samples.

EXAMPLE 15

Treatment of *B. abortus* in Guinea Pigs

Fifteen adult female guinea pigs were inoculated with *B. abortus* ATCC 23452 ($1\times10^7$CFU, I.P.). Seven days post-inoculation animals were divided into 3 groups of 5 animals each. Group 1, designated Controls, received no treatment. Group 2 received aqueous streptomycin sulfate, I.P. injections (0.2 ml) at 10 mg/kg body weight on day 7 and 10 post-inoculation with *B. abortus*. Group 3 received SPLVs containing streptomycin sulfate I.P. injections (0.2 ml) at 10 mg/kg body weight on days 7 and 10 post-inoculation with *B. abortus*. On day 14 post-inoculation with *B. abortus*, all animals were sacrificed and spleens were removed, aseptically homogenized and serially diluted onto brucella agar for silation of *B. abortus*. Results of surviving *B. abortus* per spleen after 4 days incubation, are shown in FIG. 3. Only SPLVs containing streptomycin were effective in eliminating *B. abortus* residing within guinea pig spleen. In animals receiving aqueous streptomycin or no treatment, viable *B. abortus* bacteria were identified.

EXAMPLE 16

Treatment of *B. abortus* Infection in Cows

Nine heavily infected animals were utilized in this experiment. *B. abortus* bacterial isolations from milk and vaginal swabbings became and remained negative for six weeks following treatment with SPLVs containing streptomycin. When infection reoccurred in these animals, bacterial isolations were found only in quadrants of the udder which were positive prior to treatment.

Nine cross-bred (hereford-jersey-Brangus), 22-month old, non-gravid, confirmed *B. abortus* culture-positive cows were used. At least 4 months prior to the initiation of the study, the animals were experimentally challenged per conjunctivum with $1\times10^7$CFU of *B. abortus* Strain 2308 during mid-gestation, which resulted in abortion and/or *B. abortus* culture positive lacteal or uterine secretions and/or fetal tissues.

Cows were maintained in individual isolation stalls and separated into three groups. Treatment comprised a two-dose regimen, spaced 3 days apart, as follows: (1) 3 cows were injected intraperitoneally with physiological saline. (2) 3 cows were injected intraperitoneally with aqueous antibiotic (streptomycin at 10 mg/kg body weight) plus preformed buffer-filled SPLVs. (3) 3 dows were injected intraperitonealy with SPLV-entrapped streptomycin (10 mg/kg body weight). The total volume per injection was 100 ml per animal.

During the first 2 months duplicate bacteriologic cultures of lacteal and uterine secretions were performed weekly providing secretions were obtainable. Then, all 5 cows were euthanized with an overdose of sodium pentabarbitol, and the following organs were collected in duplicate for bacteriologic cultures: (1) lymph nodes: left and right atlantal, left and right suprapharyngeal, left and right mandibular, left and right parotid, left and right prescapular, left and right prefemoral, left and right axillary, left and right popliteal, left and right internal iliac, left and right supramammary, left and right renal, bronchial, mediastinal, mesenteric, and hepatic; (2) glands: all four quarters of mammary gland, left and right adrenal glands and thymus (if present); (3) organs and other tissues: spleen, liver, left and right horn of uterus, cervix, vagina, kidney and tonsil.

After necropsy, all tissues were frozen and maintained at −70° C. while in transport. Tissues were thawed, alcohol flamed, and aseptically trimmed prior to weighing. Once weights were recorded (0.2 to 1.0 grams), the tissue was homogenized in 1 ml of sterile saline and serially diluted with sterile saline to $1:10^{-10}$ of initial homogenate suspension. Aliquots (20 ul) of each dilution from serial suspensions were plated onto brucella agar and placed in 30° C. incubation. Duplicate determinations were performed for each tissue.

Plates were read daily and scored for bacterial growth. All colonies appearing prior to 3 days were isolated, passaged, and gram stained to determine identity. On days 5, 6 and 7 during incubation colonies with morphology, growth, and gram staining characteristics consistent with *B. abortus* were counted; the CFU per gram tissue was then determined. Representative colonies were repassaged for bacterial confirmation of *B. abortus*.

Bacteriologic isolations were done on all tissue samples and quantitation of bacteria per gram of tissue were calculated. The results from four animals—one placebo control and three animals treated with SPLV-entrapped streptomycin—are presented in Table VIII.

TABLE II

STABILITY OF EGG PHOSPHATIDYLCHOLINE SPLVs AFTER STORAGE IN SEALED CONTAINERS AT 4° C. FOR 4½ MONTHS[a]

| Entrapped Drug | Initial Entrapment % | Leakage Into Supernatant[b] | Bioavailability of Entrapped Drug (%) |
|---|---|---|---|
| Streptomycin Sulfate | 34.1 | 0 | 97 |
| Spectinomycin | 37.2 | 0 | 84 |
| Chloramphenicol | 35.2 | 0 | 89 |
| Oxytetracycline | 18.8 | 0 | 91 |
| Erythromycin | 0.4 | 0 | 97 |
| Sulfamerazine | 6.3 | 0 | 93 |

[a]SPLVs were prepared using 127 μM egg phosphatidylcholine (EPC) and 25 μM drug. At the end of 4½ months storage at 4° C. the SPLVs were separated from storage buffer by centrifugation. Serial dilutions of the SPLV contents and the supernatant were applied to bacterial lawns in order to determine bioactivity as compared to standard dilutions of antibiotic.
[b]0 indicates below detectable levels

TABLE III

COLONY-FORMING UNITS OF INTRACELLULAR BRUCELLA ISOLATED AFTER TREATMENT OF INFECTED MACROPHAGES WITH SPLVS CONTAINING STREPTOMYCIN

| | *B. canis*[a] | *B. abortus*[b] |
|---|---|---|
| Controls | $2.6 \pm 1.13 \times 10^3$ | $3.1 \pm 0.81 \times 10^4$ |
| Buffer-filled SPLVs | $2.82 \pm 0.10 \times 10^3$ | $2.9 \pm 0.17 \times 10^4$ |
| Free Streptomycin[c] | $3.11 \pm 0.40 \times 10^3$ | $3.3 \pm 0.25 \times 10^4$ |
| Streptomycin Plus Buffer-filled SPLVs[c] | $2.76 \pm 0.20 \times 10^3$ | $2.8 \pm 0.42 \times 10^4$ |
| SPLV-Entrapped Streptomycin[c] | 0 | 0 |

[a]Colony forming units (CFU) of *B. canis* (mean ± SD of 12 replicates) isolated from equal numbers of previously infected mouse ($C_{57}Blk$) peritoneal macrophages.
[b]CFU of *B. abortus* (mean ± SD of 12 replicates) isolated from equal numbers of previously infected guinea pig peritoneal macrophages.
[c]Concentration of streptomycin 1 mg/ml.

TABLE IV

EFFECT OF A SINGLE TREATMENT[a] OF *B. CANIS* INFECTED MICE WITH VARIOUS CONCENTRATIONS OF FREE OR SPLV-ENTRAPPED STREPTOMYCIN

| | Colony-Forming Units *B. Canis* Per Spleen[b] | |
|---|---|---|
| | No Treatment | Buffer-Filled SPLVs |
| Control | $3.46 \times 10^6 \pm 2.7 \times 10^6$ | $4.1 \times 10^6 \pm 0.66 \times 10^6$ |
| Streptomycin Concentration (mg/kg body weight) | Free Streptomycin | SPLV-Entrapped Streptomycin |
| 1 | $1.5 \pm 0.45 \times 10^6$ | $1.01 \pm 0.25 \times 10^3$ |
| 5 | $2.12 \pm 1.71 \times 10^5$ | $1.52 \pm 0.131 \times 10^4$ |
| 10 | $9.66 \pm 3.68 \times 10^4$ | $1.32 \pm 1.00 \times 10^4$ |

[a]I.P injection in total of 0.2 ml (sterile saline).
[b]Surviving *B. canis* was determined as the number of CFU isolated per spleen and is expressed as mean ± S.D. of 10 animals per experiment (triplicate experiments).

TABLE V

COMPARISON OF VARIOUS ANIBIOTICS ON KILLING OF *B. CANIS* IN VIVO AFTER TWO TREATMENTS[a]

| | Colony-Forming Units *B. Canis* Per Spleen[b] | |
|---|---|---|
| | Aqueous Solutions | SPLV-Entrapped Antibiotic |
| Untreated | $3.93 \pm 1.51 \times 10^6$ | $4.66 \pm 0.87 \times 10^6$ |
| Antibiotic[c] | | |
| Dihydrostreptomycin | $1.13 \pm 0.30 \times 10^5$ | 0 |
| Gentamycin | $7.06 \pm 2.53 \times 10^5$ | 0 |
| Kanamycin | $2.72 \pm 0.91 \times 10^5$ | 0 |
| Streptomycin | $1.01 \pm 0.17 \times 10^5$ | 0 |

[a]Intraperitoneal treatments, 10 mg/kg body weight, were spaced at 3 day intervals. Controls received no treatment.
[b]Surviving *B. canis* per organ was determined as the number of CFU isolated per spleen and expressed as the mean ± S.D. of 5 animals per groups (duplicate determinations per animal).
[c]Antibiotics effective in killing *B. canis* in suspension culture.

TABLE VI

RESULTS OF CULTURES AND SERLOGICAL TESTING IN *B. CANIS* INFECTED DOGS SUBJECTED TO A TWO TREATMENT ANTIBIOTIC REGIMEN[a]

| Days After Infection with | Control | | | | Streptomycin[b] | | | | SPLV-Entrapped Streptomycin[c] | | | |
|---|---|---|---|---|---|---|---|---|---|---|---|---|
| *B. Canis* | R | M | B | V | R | M | B | V | R | M | B | V |
| Pre-treatment | | | | | | | | | | | | |
| 0 | 0 | 0 | 0 | 0 | 0 | 0 | 0 | 0 | 0 | 0 | 0 | 0 |
| 2 | ND | ND | + | + | ND | ND | + | 0 | ND | ND | + | + |
| 4 | ND | ND | + | + | ND | ND | + | + | ND | ND | + | + |
| Post-treatment | | | | | | | | | | | | |
| 8 | 0 | 0 | 0 | + | 0 | 0 | + | 0 | 0 | 0 | 0 | 0 |

TABLE VI-continued

RESULTS OF CULTURES AND SERLOGICAL TESTING IN *B. CANIS* INFECTED DOGS SUBJECTED TO A TWO TREATMENT ANTIBIOTIC REGIMEN[a]

| Days After Infection with B. Canis | Control | | | | Streptomycin[b] | | | | SPLV-Entrapped Streptomycin[c] | | | |
|---|---|---|---|---|---|---|---|---|---|---|---|---|
| | R | M | B | V | R | M | B | V | R | M | B | V |
| 10 | 0 | 0 | 0 | + | 0 | 0 | 0 | + | 0 | 0 | 0 | 0 |
| 21 | 1.5 | 2 | + | + | 1 | 2 | + | + | 0 | 0 | 0 | 0 |

[a]R (rapid slide agglutination test) indicates the reciprocal of serum titer to *B. canis* antigen ($\times 10^2$); 0 = no detectable titer.
M (2-mercaptoethanol tube agglutination test) indicates the reciprocal of serum titer to *B. canis* antigen ($\times 10^2$); 0 = no detectable titer.
In B (blood culture) and V (vaginal culture) on brucella agar: + = detection of greater than or equal to 1 CFU; 0 = no colonies detected. Controls received no treatment.
[b]Streptomycin sulfate (aqueous) 10 mg/kg body weight, I.P.
[c]SPLVs containing streptomycn sulfate 10 mg/kg body weight, I.P.

TABLE VII

RESULTS OF CULTURES FROM TISSUE SAMPLES IN *B. CANIS* INFECTED DOGS SUBJECTED TO A TWO TREATMENT ANTIBIOTIC REGIMEN[a]

| Tissue[b] | SPLVs Containing Streptomycin[c] | Streptomycin[d] | Control[e] |
|---|---|---|---|
| Whole blood | 0 | + | + |
| Vaginal swab | 0 | + | + |
| Lungs | 0 | + | + |
| Spleen | 0 | + | + |
| Synovial fluid | N.D. | 0 | 0 |
| Uterus | 0 | + | + |
| Ovary | 0 | + | + |
| Popliteal lymph node | N.D. | + | + |
| Salivary gland | 0 | 0 | 0 |
| Tonsil | 0 | + | + |
| Mediastinal lymph node | 0 | N.D. | + |
| Mesenteric lymph node | N.D. | 0 | 0 |
| Bone marrow | 0 | + | + |
| Superficial cervical lymph node | N.D. | N.D. | + |
| Axillary lymph node | 0 | + | + |

[a]Animals treated on day 7 and 10 post-infection.
[b]Samples taken at necropsy were serially diluted on brucella agar; + = equal to or greater than 1 CFU; 0 = no colonies.
[c]SPLVs containing streptomycin sulfate, 10 mg/kg body weight, I.P.
[d]Streptomycin sulfate (aqueous), 10 mg/kg body weight, I.P.
[e]Controls received no treatment.

TABLE VIII

RESULTS OF CULTURES FROM TISSUE SAMPLES OF *B. ABORTUS* INFECTED COWS

| Tissue | Untreated Control | SPLV-Entrapped Streptomycin | | |
|---|---|---|---|---|
| | | 1 | 2 | 3 |
| Adrenal gland L | 0 | 0 | 0 | 0 |
| Adrenal gland R | ++ | 0 | 0 | + |
| Atlantal LN R | ++ | + | 0 | + |
| Atlantal LN L | 0 | 0 | 0 | + |
| Axillary LN R | +++ | 0 | + | 0 |
| Axillary LN L | ++ | 0 | 0 | 0 |
| Bronchial LN | 0 | 0 | 0 | 0 |
| Cervix | 0 | 0 | 0 | 0 |
| Hepatic LN | ++++ | 0 | 0 | 0 |
| Horn of Uterus L | 0 | 0 | 0 | + |
| Horn of Uterus R | 0 | 0 | 0 | 0 |
| Int. Illiac LN R | ++ | 0 | 0 | 0 |
| Int. Illiac LN L | ++++ | 0 | + | 0 |
| Kidney | 0 | 0 | 0 | 0 |
| Liver | 0 | 0 | 0 | 0 |
| Lung | 0 | 0 | 0 | 0 |
| Mammary Gland LF | 0 | + | + | 0 |
| Mammary Gland LR | 0 | 0 | 0 | + |
| Mammary Gland RF | ++ | 0 | 0 | 0 |
| Mammary Gland RR | ++ | 0 | 0 | 0 |
| Mandibular LN R | +++ | 0 | 0 | 0 |
| Mandibular LN L | +++ | 0 | 0 | 0 |
| Mediastinal LN | ++ | 0 | + | 0 |
| Mesenteric LN | +++ | 0 | 0 | 0 |
| Parotid LN L | +++ | 0 | 0 | 0 |
| Parotid LN R | +++ | 0 | 0 | 0 |
| Popliteal LN L | + | 0 | 0 | 0 |
| Popliteal LN R | + | 0 | 0 | 0 |
| Prefemoral LN L | + | 0 | 0 | 0 |
| Prefemoral LN R | 0 | 0 | 0 | 0 |
| Prescapular LN L | 0 | 0 | 0 | + |
| Prescapular LN R | ++++ | 0 | 0 | 0 |
| Renal LN | 0 | 0 | 0 | 0 |
| Spleen | +++ | 0 | 0 | 0 |
| Supramammary LN L | +++ | + | 0 | 0 |
| Supramammary LN R | 0 | 0 | 0 | 0 |
| Suprapharangeal LN L | + | 0 | 0 | 0 |
| Suprapharangeal LN R | 0 | 0 | 0 | 0 |
| Thymus | 0 | 0 | 0 | 0 |
| Vagina | +++ | 0 | 0 | 0 |

0 No detectable bacteria by culture of 0.3–1 gm of tissue.
+ Less than 200 colonies/gm tissue.
++ More than 300 colonies/gm.
+++ More than 1,000 colonies/gm.
++++ More than 100,000 colonies/gm.

We claim:

1. A method of treating infections in an animal by administration of a therapeutically effective amount of aminoglycoside in liposome form by intramammary infusion.

2. A method of treating Brucella spp. infections in an animal by administration of a therapeutically effective amount of aminoglycoside in liposome form by intramammary infusion.

3. The method of claim 2 wherein the aminoglycoside is streptomycin.

4. The method of claim 3 wherein the streptomycin is administered at from about 35 to about 50 mg/kg body weight.

5. The method of claim 3 wherein the streptomycin is administered in a dose regimen of about 2 to about 5 doses.

6. The method of claim 3 wherein the liposomes comprise at least about equal amounts of lipid and streptomycin sulfate (w/w).

7. The method of claim 2 further comprising administration of a therapeutically effective amount of a tetracycline.

8. The method of claim 7 wherein the tetracycline is oxytetracycline.

9. The method of claim 8 wherein the oxytetracycline is administered at from about 10 to about 30 mg/kg body weight.

10. The method of claim 2 wherein the liposomes are stable plurilamellar vesicles.

11. The method of claim 10 wherein the liposomes comprise phosphatidylcholine.

12. A method of administering a therapeutic agent to a proximal mammary lymph node of an animal comprising intramammary infusion of said therapeutic agent in liposome form.

13. The method of claim 12 wherein the therapeutic agent is an anti-infective agent.

14. The method of claim 13 wherein the anti-infective agent is an imidazole.

15. The method of claim 13 wherein the anti-infective agent is a $\beta$-lactam.

16. The method of claim 12 wherein the therapeutic agent is an antineoplastic agent.

17. The method of claim 16 wherein the antineoplastic agent is doxorubicin.

18. The method of claim 16 wherein the antineoplastic agent is cisplatin.

19. The method of claim 16 wherein the antineoplastic agent is 5-fluorouracil

20. The method of claim 12 wherein the liposomes are stable plurilamellar vesicles.

21. The method of claim 12 wherein the liposomes comprise phosphatidylcholine.

* * * * *